(12) United States Patent
Bonnett et al.

(10) Patent No.: US 8,580,835 B2
(45) Date of Patent: Nov. 12, 2013

(54) SOLID FORMS OF A MICROBIOCIDE

(75) Inventors: Paul Edward Bonnett, Greensboro, NC (US); Neil George, Bracknell (GB); Ian Kevin Jones, Bracknell (GB); Shailesh Shah, Zürich (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 954 days.

(21) Appl. No.: 12/531,503

(22) PCT Filed: Feb. 19, 2008

(86) PCT No.: PCT/EP2008/001259
§ 371 (c)(1),
(2), (4) Date: Feb. 3, 2010

(87) PCT Pub. No.: WO2008/113447
PCT Pub. Date: Sep. 25, 2008

(65) Prior Publication Data
US 2013/0203832 A1     Aug. 8, 2013

(30) Foreign Application Priority Data

Mar. 16, 2007 (EP) ..................................... 07005456

(51) Int. Cl.
*C07D 231/14* (2006.01)
(52) U.S. Cl.
USPC ....................................... 514/406; 548/374.1

(58) Field of Classification Search
None
See application file for complete search history.

(56) References Cited

U.S. PATENT DOCUMENTS 7,598,395 B2 * 10/2009 Ehrenfreund et al. ..... 548/356.1

FOREIGN PATENT DOCUMENTS

| WO | 2004035589 | 4/2004 |
|---|---|---|
| WO | 2006/037632 | 4/2006 |
| WO | 2007031323 | 3/2007 |

OTHER PUBLICATIONS

Morissette, S.L. et al., "High-throughput crystallization: polymorphs, salts, co-crystals and solvates of pharmaceutical solids", Advanced Drug Delivery Reviews, vol. 56 (2004) pp. 275-300.
Khankari, R.K. and Grant, D.J.W., "Pharmaceutical hydrates", Thermochimica Acta, vol. 248, pp. 61-79 (1995).
Vippagunta, S.R. et al., "Crystalline solids", Advance Drug Delivery Reviews, vol. 48 (2001) pp. 3-26.

* cited by examiner

*Primary Examiner* — Kamal Saeed
(74) *Attorney, Agent, or Firm* — R. Kody Jones (57) ABSTRACT

The present invention relates to novel solid forms of 3-difluoromethyl-1-methyl-1H-pyrazole-4-carboxylic acid (9-isopropyl-1,2,3,4-tetrahydro-1,4-methano-naphthalen-5-yl)-amide, such as crystal modifications and hydrates, compositions comprising these novel solid forms and to the use thereof in the control of disease infestation in cultivated plants.

13 Claims, 8 Drawing Sheets

FIG. 1

X-ray powder diffraction pattern of crystal modification C

FIG. 2

Raman Spectrum of crystal modification C

FIG. 3
DSC-thermogramm of crystal modification C

FIG. 4
X-ray powder diffraction pattern of crystal modification I

FIG. 5

Raman Spectrum of crystal modification I

FIG. 6

DCS-thermogramm of crystal modification I

FIG. 7

X-ray powder diffraction pattern of the monohydrate in form A

FIG. 8

Raman Spectrum of the monohydrate in form A

FIG. 9

DCS-thermogramm of the monohydrate in form A

FIG. 10a

X-ray powder diffraction pattern of mixture-product (syn/anti ratio 84:16)

FIG. 10b

Overlay of x-ray powder diffraction patterns of mixture-product (syn/anti ratio 84:16) and pure syn-/anti-compounds

FIG. 11

DCS-thermogramm of the mixture-product (syn/anti-ratio 84:16)

FIG. 12a

X-ray powder diffraction pattern of mixture-product (syn/anti ratio 88:12)

FIG. 12b

Overlay of x-ray powder diffraction patterns of mixture-product (syn/anti ratio 84:16) and pure syn-/anti-compounds

FIG. 13

DCS-thermogramm of the mixture-product (syn/anti-ratio 88:12)

SOLID FORMS OF A MICROBIOCIDE

This application is a 371 of International Application No. PCT/EP2008/001259 filed Feb. 19, 2008, which claims priority to EP 07005456.4 filed Mar. 16, 2007, the contents of which are incorporated herein by reference.

The present invention relates to novel solid forms of 3-difluoromethyl-1-methyl-1H-pyrazole-4-carboxylic acid (9-isopropyl-1,2,3,4-tetrahydro-1,4-methano-naphthalen-5-yl)-amide, such as crystal modifications and hydrates, compositions comprising these novel solid forms and to the use thereof in the control of disease infestation in cultivated plants.

The above-mentioned amide is a valuable fungicide and is described, for example, in WO 04/35589 and WO 06/37632.

3-Difluoromethyl-1-methyl-1H-pyrazole-4-carboxylic acid (9-isopropyl-1,2,3,4-tetrahydro-1,4-methano-naphthalen-5-yl)-amide has the structure of the formula (I) and is herein also referred to as "compound of formula (I)":

The compound of formula (I) can occur in 4 stereoisomeric forms, shown as two pairs of enantiomers of formulae syn1/syn2 and anti1/anti2 respectively:

According to the invention "racemic syn-3-difluoromethyl-1-methyl-1H-pyrazole-4-carboxylic acid (9-isopropyl-1,2,3,4-tetrahydro-1,4-methano-naphthalen-5-yl)-amide" or "racemic syn-compound of formula (I)" means a racemic mixture of compounds of formula syn1 and syn2.

According to the invention "racemic anti-3-difluoromethyl-1-methyl-1H-pyrazole-4-carboxylic acid (9-isopropyl-1,2,3,4-tetrahydro-1,4-methano-naphthalen-5-yl)-amide" or "racemic anti-compound of formula (I)" means a racemic mixture of compounds anti1 and anti2.

Novel Polymorph of the Racemic Syn-Compound of Formula (I) ("Modification C"):

Crystalline material of the racemic syn-compound of formula (I) having a single melting point of 110-112° C. (diastereomeric purity: 90%) is disclosed in WO 04/35589. This crystalline material will be herein referred to as "crystal modification A of the of racemic syn-compound of formula (I)". A second crystalline form of the racemic syn-compound of formula (I) is disclosed in PCT/EP2006/00898 and will be herein referred to as "crystal modification B of the racemic syn-compound of formula (I)".

Amorphous material being a mixture of syn- and anti-compounds of formula (I) in a syn/anti-ratio of 35:65 is disclosed in WO 04/35589.

Various crystal modifications of chemical compounds can exhibit very different physical properties, which may lead to unforseeable problems during technical preparation and processing of these compounds. The characteristics of crystal modifications frequently have a crucial influence on separating ability (filtration), stirrability (crystal shape), surface activity (foaming), rate of drying, solubility, quality, formulating ability, storage stability and bioefficacy of, for example, pharmaceutically and agrochemically active compounds. For example, the grinding and formulating properties (e.g. granulating, milling, mixing, dissolution) of products may be completely different, depending on the respective modification. Since, depending on the envisaged formulating process, different physical properties of the respective products are of importance, it is especially advantageous to find the optimally suited crystal form for the respective formulating process. Furthermore, a modification can suddenly transform into another undesired modification under certain thermodynamic conditions which could lead, for example, to a decreased storage stability of a formulated agrochemical material. The number of polymorphic states of a chemical compound is unpredictable. The most stable polymorphic state may not form because the rate of formation of new crystals from a solution may be extremely slow.

It is therefore the aim of the present invention to specifically provide novel crystal modifications of the racemic syn-compound of formula (I) with good properties in relation to the formulation of the active ingredient and its storability either as solid material or in typical formulations used in agrochemistry, such as a suspension concentrate (SC).

The present invention relates to crystal modification C of the racemic syn-compound of formula (I) ("modification C"), wherein said crystal modification is characterized by an x-ray powder diffraction pattern, expressed in terms of d-spacings and relative intensities, wherein said x-ray powder diffraction pattern comprises the following characteristic lines: 13.74 Å (strong), 7.95 Å (weak), 6.94 Å (medium), 6.04 Å (weak), 4.43 Å (medium) and 3.72 Å (strong). The x-ray powder diffraction pattern has been obtained by using a Bruker-AXS D8 Advanced Powder X-ray diffractometer, source: Cu Kα1.

Modification C of the racemic syn-compound of formula (I) differs from modifications A and B with respect to thermodynamic stability, physical parameters, such as the absorption pattern of IR and Raman spectra, in x-ray structure investigations and in their solubility in water or other commonly used liquid carriers in agrochemical formulations.

Modification C has significant advantages compared with modification A. Thus, for example, DSC (differential scanning calometry), solubility tests and other experiments, have shown that modification C surprisingly has substantially better thermodynamic stability than modification A. For example, the water solubility of modification C is lower than the water solubility of modification A over relevant temperature ranges. In aqueous suspensions the polymorph with the lowest solubility is most stable. A polymorph with a higher solubility is unstable, because the surrounding water phase will be supersaturated relative to the more stable polymorph leading to dissolution of the more unstable polymorph and crystallisation of the more stable polymorph. The resulting change of particle sizes could lead to a change of the stability of the formulated suspension.

It is particularly important for a fungicide that its agrochemical formulation ensures high and reproducible stability over a long period. These preconditions are fulfilled by incorporation of the racemic syn-compound of formula (I) in the form of the crystal modification C, owing to its high thermodynamic stability compared with crystal modification A. In particular, this is displayed in the suspension concentrate agrochemical dosage form. If an active ingredient is subjected to a conversion process, this may readily also affect the stability of this formulation.

Agrochemical active ingredients or polymorphic forms thereof which are of primary interest for development of new active ingredients are those which exhibit high stability and do not have the above-mentioned disadvantages. The modification C fulfills these preconditions.

Modification C was prepared as described in example P1 (spontaneous crystallization from solution in o-xylene). Said modification can also be prepared by using the crystallization technique laid out in example P1b) while using other solvents, such as acetonitrile, methylcyclohexane, 1-pentanol or 1,2-propandiol.

Modification C has been analyzed by x-ray powder diffraction (using a Bruker-AXS D8 Advanced Powder X-ray diffractometer, source: Cu Kα1) and an x-ray powder pattern has been obtained with characteristic lines with interplanar spacings (d values in Angstrom) of 13.74 Å (strong), 7.95 Å (weak), 6.94 Å (medium), 6.04 Å (weak), 4.43 Å (medium) and 3.72 Å (strong) (see table 1 or FIG. 1).

TABLE 1

Characterization of modification C of the racemic syn-compound of formula (I) (x-ray powder pattern)

| 2-Theta | d-Spacing (Å) | Strength |
|---------|---------------|----------|
| 6.44    | 13.74         | strong   |
| 11.17   | 7.95          | weak     |
| 11.54   | 7.70          | medium   |
| 12.82   | 6.94          | medium   |
| 14.78   | 6.04          | weak     |
| 16.35   | 5.47          | strong   |
| 17.00   | 5.27          | medium   |
| 18.41   | 4.88          | weak     |
| 20.37   | 4.43          | medium   |
| 22.39   | 4.04          | strong   |
| 24.45   | 3.72          | strong   |
| 25.43   | 3.59          | medium   |

In contrast, modifications A and B have x-ray powder patterns with different characteristic lines: 21.98 Å (medium), 10.81 Å (weak), 8.79 Å (weak), 6.51 Å (weak), 4.65 Å (medium) and 4.20 Å (medium) (modification A); and 13.42 Å (strong), 9.76 Å (medium), 6.93 Å (medium), 6.74 Å (medium), 4.79 Å (medium), 4.73 Å (medium), and 3.66 Å (medium) (modification B). Both patterns are described in PCT/EP2006/00898 (see tables 7-8 and FIGS. 1-2). The x-ray powder diffraction patterns have been obtained as described above for modifaction C.

Figure 2:
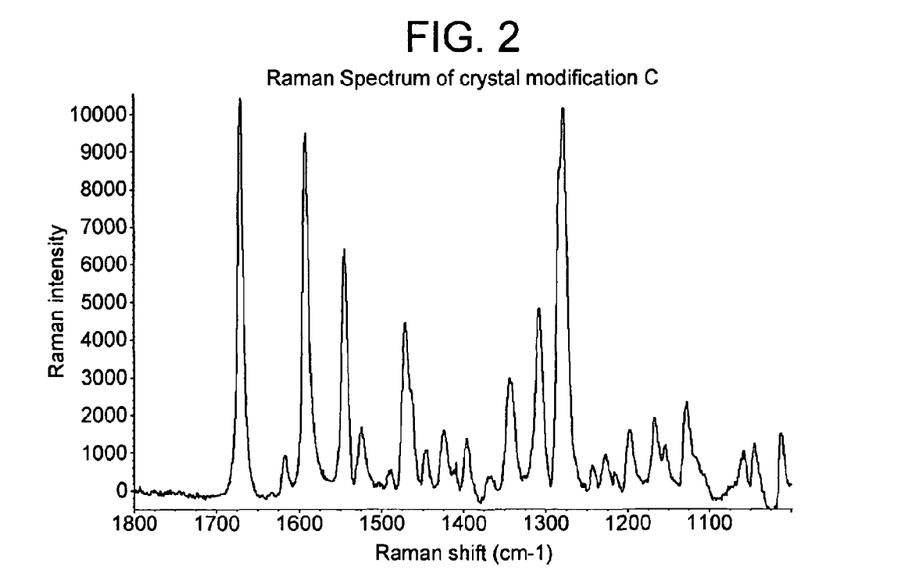
FIG. 2 shows the Raman spectrum and FIG. 3 shows the DSC-plot of crystal modification C of the racemic syn-compound of formula (I) as prepared in example P1.

In the Raman spectrum modification C differs from modifications A and B in the shape and in the relative intensity of many bands (see FIG. 2). The Raman spectra of modifications A and B are depicted in PCT/EP2006/00898, FIGS. 4 and 3. For the recording of all Raman Spectra, the apparatus Thermo Electron Almega Raman Microscope (785 nm, High Resolution settings) has been used.

Figure 3:
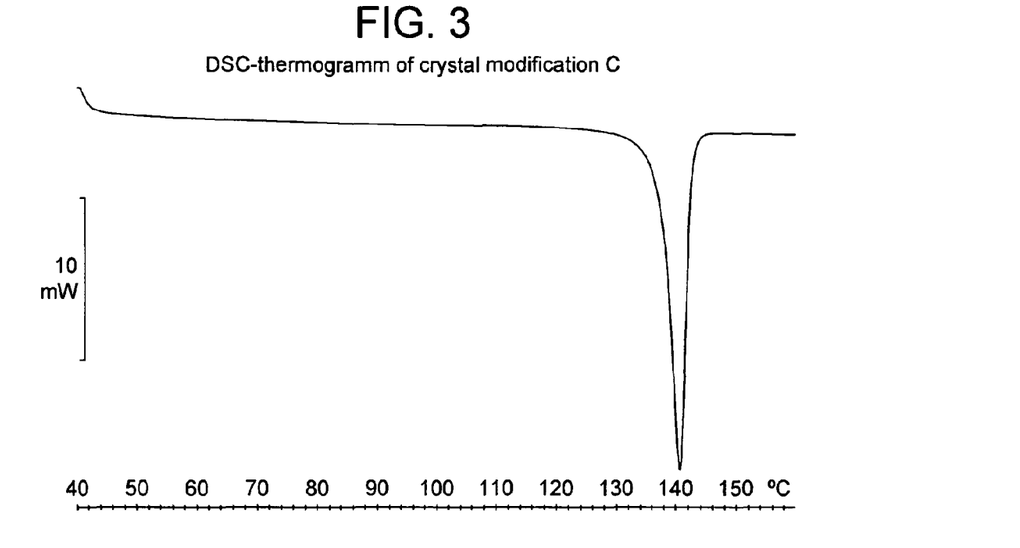

Characteristic for modification C is also the thermogram in differential scanning calorimetry ("DSC") (see FIG. 3). It has an endothermic peak typically in the range from 130° C. to 142° C., but this will depend on purity. For example, crystal modification C in pure form has typically a peak temperature of 141° C. and an endothermic signal typically around 83 J/g. This thermogram is characteristically different from the thermograms of modifications A and B. Modification A has an endothermic peak at about 112° C. and an endothermic signal of 76; modification B has a peak at about 128° C. and a signal of 90 J/g (see PCT/EP2006/00898, FIGS. 5-6). All measurements were carried out on a Metier Toledo 820 DSC in a closed, but not sealed, pan with a heating rate of 10 K/minute. The typical sample quantity is about 5 mg.

The present invention preferably relates to crystal modification C of the racemic syn-compound of formula (I), wherein said crystal modification is characterized by an x-ray powder diffraction pattern, expressed in terms of d-spacings and relative intensities, wherein said an x-ray powder diffraction pattern comprises the following characteristic lines: 13.74 Å (strong), 7.95 Å (weak), 7.70 Å (medium), 6.94 Å (medium), 6.04 Å (weak), 5.47 Å (strong), 5.27 Å (medium), 4.88 Å (weak), 4.43 Å (medium), 4.04 Å (strong), 3.72 Å (strong) and 3.59 Å (medium).

Figure 1:
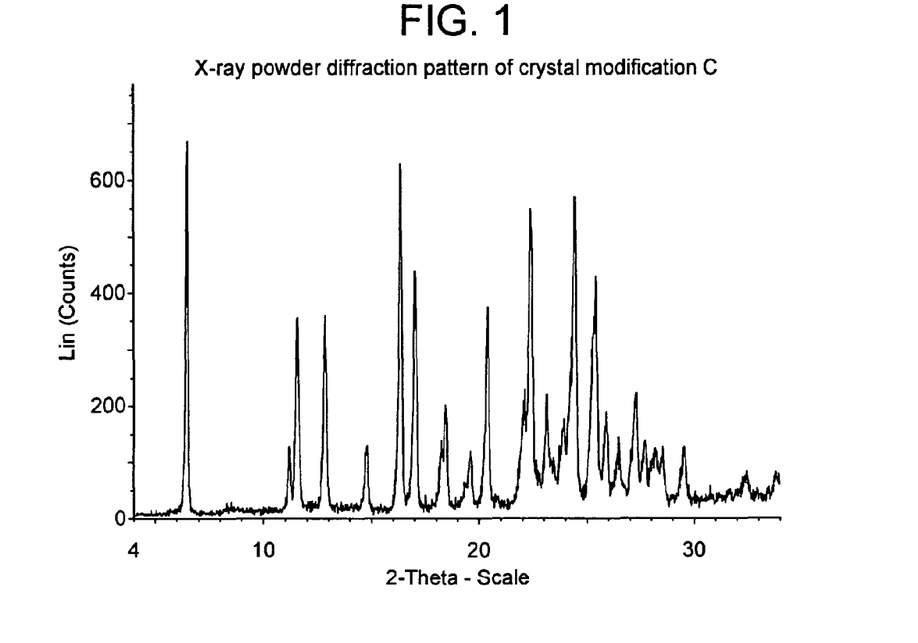

The present invention preferably relates to the crystal modification C of the racemic syn-compound of formula (I), wherein said crystal modification is characterized having the x-ray powder diffraction pattern depicted in FIG. 1.

In one embodiment of the invention, the crystal modification C of the racemic syn-compound of formula (I) has in the thermogram in differential scanning calorimetry an endothermic signal with a peak in the range from 130° C. to 142° C.

In one embodiment of the invention, the crystal modification C of the racemic syn-compound of formula (I) is in substantially pure form. According to the invention "substantially pure" means preferably at least 70% by weight of crystal modification C of the racemic syn-compound of formula (I), more preferably at least 75% by weight, even more preferably at least 80% by weight. The chemical nature of the material, which is not the crystal modification C of the racemic syn-compound of formula (I), will depend on the production and/or purification method and at least part of it can be, for example, the racemic anti-compound of formula (I), which can be present in solid solution in the crystal matrix of the syn-compound or in the form of individual crystalline or amorphous material.

In another embodiment of the present invention, the crystal modification C of the racemic syn-compound of formula (I) is in pure form. According to the invention "pure" means at least 90% by weight of crystal modification C of the racemic syn-compound of formula (I), more preferably at least 95% by weight, even more preferably at least 98% by weight.

Novel Polymorph of the Racemic Anti-Compound of Formula (I) ("Modification I"):

As laid out above, WO 04/35589 discloses an anti-enriched amorphous material of compounds of formula (I) which has an anti/syn-ratio of 65:35. Anti-enriched crystalline material is yet unknown.

The only crystalline material of the compound of formula (I), which is known, is highly syn-enriched. As laid out above, this material is either crystal modification A or B of the racemic syn-compound of formula (I) and is known from WO 04/35589 and PCT/EP2006/00898. Both materials have diastereomeric syn-purities of around 75% or above. Using x-ray or DSC analysis on those materials, no further crystal form was detected. This suggests that in these materials all anti-compounds are either in solid solution in the crystal matrices of the syn-compounds or in the form of amorphous material.

For anti-enriched material there is therefore the need to provide novel crystal modifications with good properties in relation to the formulation of the active ingredient and its storability either as solid material or in typical formulations used in agrochemistry, such as a suspension concentrate (SC).

Amorphous material has several drawbacks. At temperature ranges which are typical for storage of agrochemicals, amorphous material behaves as an undercooled supersaturated liquid. Out of this reason, it is thermodynamically unstable and will crystallize over time, i.e. it will change its physical-chemical properties. When an acitve ingredient is stored, for example as unformulated technical material or as solid formulated material (such as a water-dispersible granule-formulation, WG) this lack of storage-stability can lead to unforseeable problems during further processing of these active ingredients. Furthermore, amorphous material generally has a higher solubility in water over relevant temperature ranges. In aqueous suspensions (such as SC-formulations), amorphous material is unstable, because the surrounding water phase will be supersaturated relative to more stable crystalline forms leading to dissolution of the more unstable amorphous and crystallisation of the more stable crystalline form. The resulting change of particle sizes could lead to a change of the stability of the formulated suspension. It is particularly important for a fungicide that its agrochemical formulation ensures high and reproducible stability over a long period.

The present invention relates to crystal modification I of the racemic anti-compound of formula (I) ("modification I"), wherein said crystal modification is characterized by an x-ray powder diffraction pattern, expressed in terms of d-spacings and relative intensities, wherein said x-ray powder diffraction pattern comprises the following characteristic lines: 16.19 Å (very strong), 11.77 Å (strong), 9.47 Å (medium), 5.49 Å (very strong), 5.16 Å (medium), 4.61 Å (strong) and 4.22 Å (strong). The x-ray powder diffraction pattern has been obtained by using a Bruker-AXS D8 Advanced Powder X-ray diffractometer, source: Cu Kα1.

Modification I differs from the physical state of the known anti-enriched material, which is amorphous. Modification I has the above-described significant advantages compared with the known amorphous anti-enriched material.

Agrochemical active ingredients or polymorphic forms thereof which are of primary interest for development of new active ingredients are those which exhibit high stability and do not have the above-mentioned disadvantages. The modification I of the racemic anti-compound of formula (I) fulfills these preconditions.

Modification I of the racemic anti-compound of formula (I) was prepared as described in example P2 (spontaneous crystallization from solution in hexane). Said modification can also be prepared by using the crystallization technique laid out in example P1b) while using other solvents, such as ethanol, isopropanol, 2-methylpentane, acetone, 1-pentanole, ethyl acetate, 2-methyl-2-butanol, methylcyclohexane and o-xylene.

Figure 4:
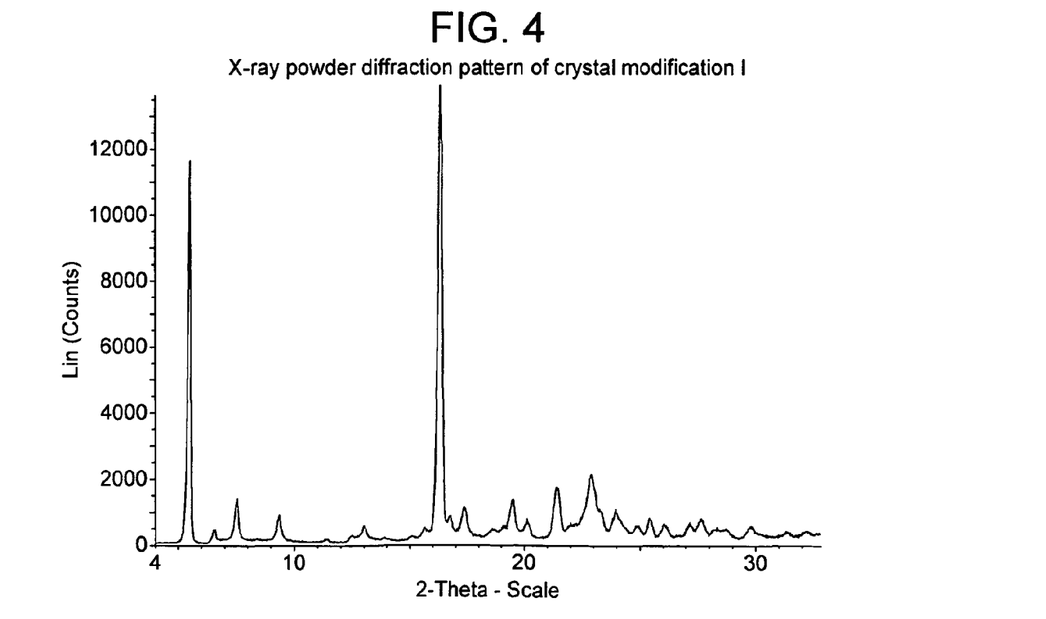

Modification I has been analyzed by x-ray powder diffraction (as described above for modification C of the racemic syn-compound of formula (I)) and a pattern has been obtained with characteristic lines with interplanar spacings (d values in Angstrom) of 16.19 Å (very strong), 11.77 Å (strong), 9.47 Å (medium), 5.49 Å (very strong), 5.16 Å (medium), 4.61 Å (strong) and 4.22 Å (strong) (see table 2 or FIG. 4).

TABLE 2

Characterization of modification I of the racemic anti-compound of formula (I) (x-ray powder pattern)

| 2-Theta | d-Spacing (Å) | Strength |
|---------|---------------|----------|
| 5.46 | 16.19 | very strong |
| 6.47 | 13.67 | weak |
| 7.52 | 11.77 | strong |
| 9.36 | 9.47 | medium |
| 13.01 | 6.84 | weak |
| 16.30 | 5.49 | very strong |
| 17.38 | 5.16 | medium |
| 19.51 | 4.61 | strong |
| 21.40 | 4.22 | strong |
| 22.93 | 3.95 | strong |
| 23.92 | 3.80 | medium |
| 25.44 | 3.59 | weak |

Figure 5:
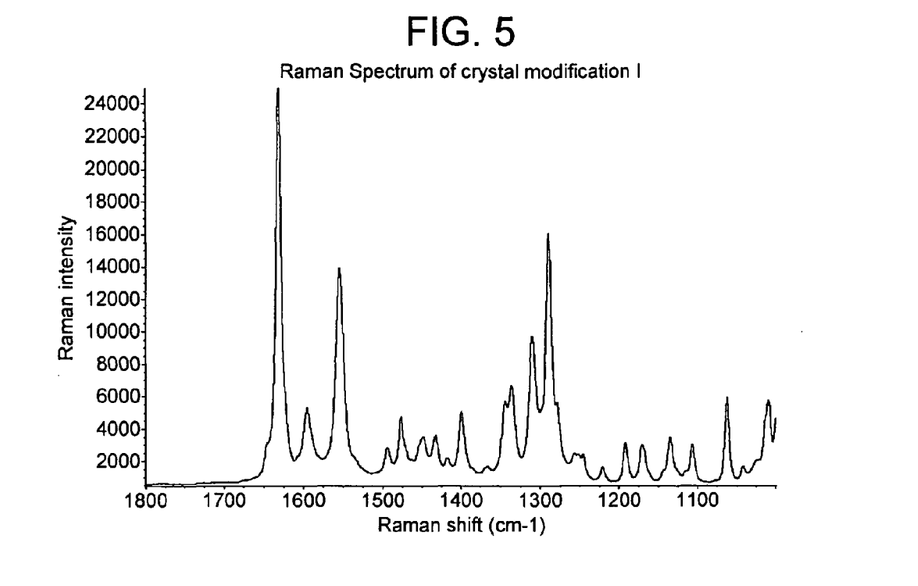
FIG. 5 shows the Raman spectrum and FIG. 6 shows the DSC-plot of crystal modification I of the racemic anti-compound of formula (I) as prepared in example P2.

The Raman spectrum of modification I also shows characteristic bands (see FIG. 5). The spectrum was recorded as described above for modification C of the racemic syn-compound of formula (I).

Figure 6:
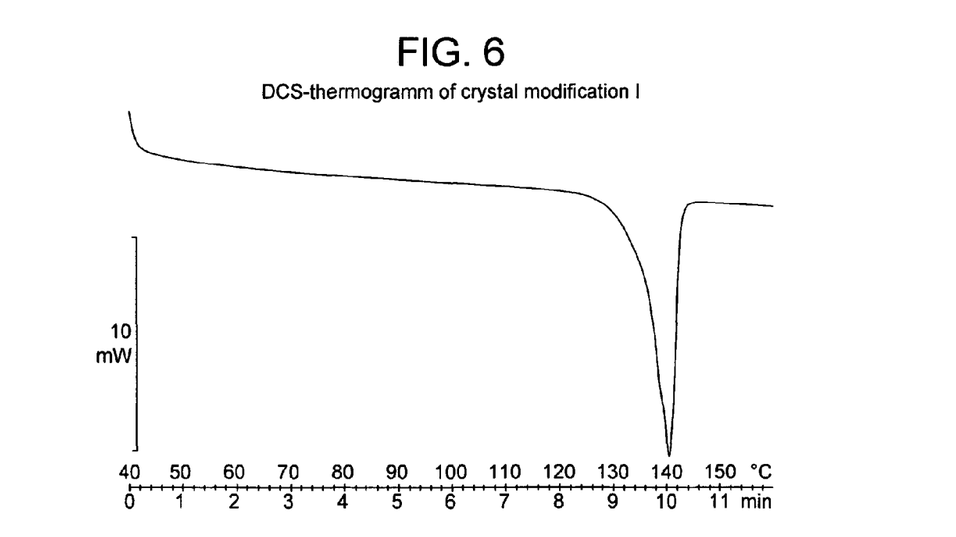

Characteristic for modification I is also the thermogram in DSC (see FIG. 6). Crystal modification I in pure form has typically an endothermic peak at 140° C. and typically an endothermic signal of around 92.3 J/g. The measurement was carried out as described above for modification C of the racemic syn-compound of formula (I).

The present invention preferably relates to crystal modification I of the racemic anti-compound of formula (I), wherein said crystal modification is characterized by an x-ray powder diffraction pattern, expressed in terms of d-spacings and relative intensities, wherein said an x-ray powder diffraction pattern comprises the following characteristic lines: 16.19 Å (very strong), 13.67 Å (weak), 11.77 Å (strong), 9.47 Å (medium), 6.84 Å (weak), 5.49 Å (very strong), 5.16 Å (medium), 4.61 Å (strong), 4.22 Å (strong), 3.95 Å (strong), 3.80 Å (medium) and 3.59 Å (weak).

The present invention preferably relates to the crystal modification I of the racemic anti-compound of formula (I), wherein said crystal modification is characterized by having the x-ray powder diffraction pattern depicted in FIG. 4.

In one embodiment of the invention, the crystal modification I of the racemic anti-compound of formula (I) is in substantially pure form. According to the invention "substantially pure" means preferably at least 75% by weight of crystal modification I of the racemic anti-compound of formula (I), more preferably at least 80% by weight. The chemical nature of the material, which is not the crystal modification I of the racemic anti-compound of formula (I), will depend on the production and/or purification method and at least part of it can be, for example the racemic syn-compound of formula (I), which can be present in solid solution in the crystal matrix of the anti-compound or in the form of individual crystalline or amorphous material.

In another embodiment of the present invention, the crystal modification I of the racemic anti-compound of formula (I) is in pure form. According to the invention "pure" means at least 90% by weight of crystal modification I of the racemic anti-compound of formula (I), more preferably at least 95% by weight, even more preferably at least 98% by weight.

Novel Monohydrate of the Racemic Anti-Compound of Formula (I) ("Monohydrate in Form A"):

The present invention further relates to a monohydrate in form A of the racemic anti-compound of formula (I), wherein said form is characterized by an x-ray powder diffraction pattern, expressed in terms of d-spacings and relative intensities, wherein said x-ray powder diffraction pattern comprises the following characteristic lines: 6.39 Å (weak), 6.08 Å (weak), 5.33 Å (strong), 4.07 Å (weak), 3.84 Å (medium) and 3.47 Å (weak). The x-ray powder diffraction pattern has been obtained by using a Bruker-AXS D8 Advanced Powder X-ray diffractometer, source: Cu Kα1.

The monohydrate in form A of the racemic anti-compound of formula (I) differs in its physical state from the physical state of all known anti-compounds, which are either anti-enriched, but amorphous, or present only in low amounts in solid solution in crystal matrices of syn-compounds as described above. The monohydrate in form A also differs from the modification I of the racemic anti-compound of formula (I) with respect to water content, thermodynamic stability, physical parameters, such as the absorption pattern of IR and Raman spectra, in x-ray structure investigations and in their solubility in water or other commonly used liquid carriers in agrochemical formulations.

The monohydrate in form A of the racemic anti-compound of formula (I) has significant advantages in terms of storage stability compared with the known amorphous anti-enriched material or even compared with the modification I. Compared with the amorphous material, the monohydrate in form A has due its crystalline state the same advantages as laid out above for modification I. This advantages are especially pronounced for aqueous suspensions (such as SC-formulations) and at storage in solid form under humid conditions, because the monohydrate in form A is much more stable under those circumstances compared with amorphous material or with the modification I.

Agrochemical active ingredients or polymorphic forms thereof which are of primary interest for development of new active ingredients are those which exhibit high stability and do not have the above-mentioned disadvantages. The monohydrate in form A fulfills these preconditions.

The monohydrate in form A of the racemic anti-compound of formula (I) was prepared as described in example P3.

Figure 7:
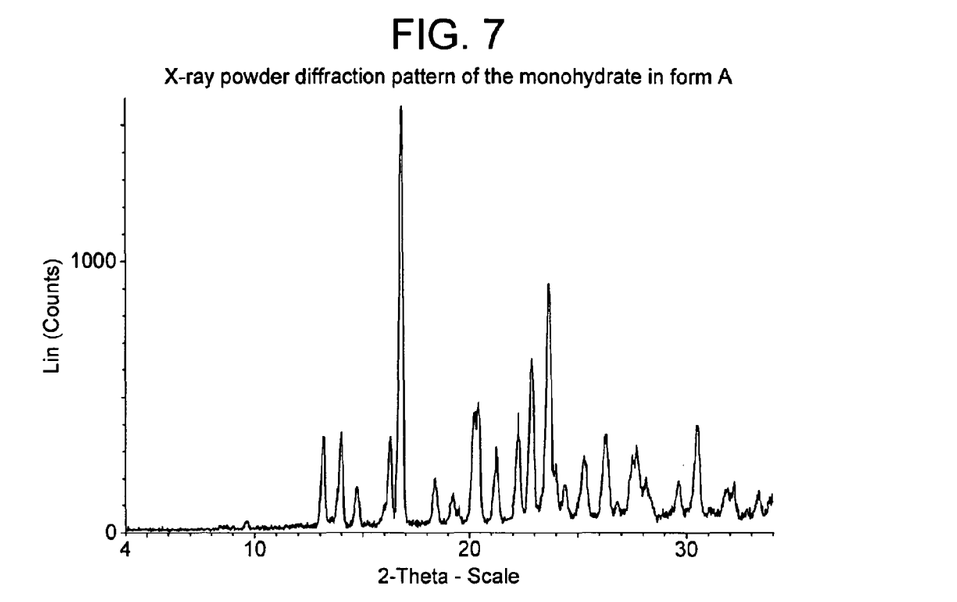

The monohydrate in form A has been analyzed by x-ray powder diffraction (as described above for modification C of the racemic syn-compound of formula (I)) and a pattern has been obtained with characteristic lines with interplanar spacings (d values in Angstrom) of 6.39 Å (weak), 6.08 Å (weak), 5.33 Å (strong), 4.07 Å (weak), 3.84 Å (medium) and 3.47 Å (weak) (see table 3 or FIG. 7).

TABLE 3

Characterization of the monohydrate in form A of the racemic anti-compound of formula (I) (x-ray powder pattern)

| 2-Theta | d-Spacing (Å) | Strength |
|---------|---------------|----------|
| 13.08 | 6.81 | weak |
| 13.96 | 6.39 | weak |
| 14.69 | 6.08 | weak |
| 16.26 | 5.50 | weak |
| 16.81 | 5.33 | strong |
| 18.34 | 4.90 | weak |
| 20.34 | 4.43 | medium |
| 21.23 | 4.25 | weak |
| 22.24 | 4.07 | weak |
| 22.88 | 3.96 | medium |
| 23.68 | 3.84 | medium |
| 25.28 | 3.61 | weak |
| 26.32 | 3.47 | weak |

In contrast, modification I has an x-ray powder pattern with different characteristic lines: 16.19 Å (very strong), 11.77 Å (strong), 9.47 Å (medium), 5.49 Å (very strong), 5.16 Å (medium), 4.61 Å (strong) and 4.22 Å (strong) (see table 2 or FIG. 4).

Figure 8:
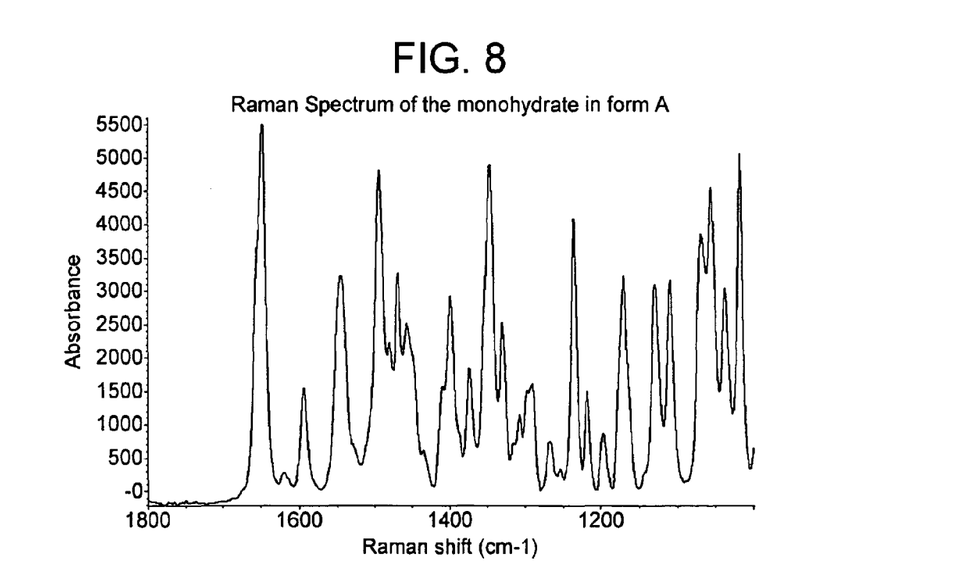
FIG. 8 shows the Raman spectrum and FIG. 9 shows the DSC-plot of the monohydrate in form A of the racemic anti-compound of formula (I) as prepared in example P3.

In the Raman spectrum the monohydrate in form A differs from modification I in the shape and in the relative intensity of many bands (see FIG. 8 in comparison with FIG. 5). As mentioned above, the spectra were recorded as described for modification C of the racemic syn-compound of formula (I).

Figure 9:
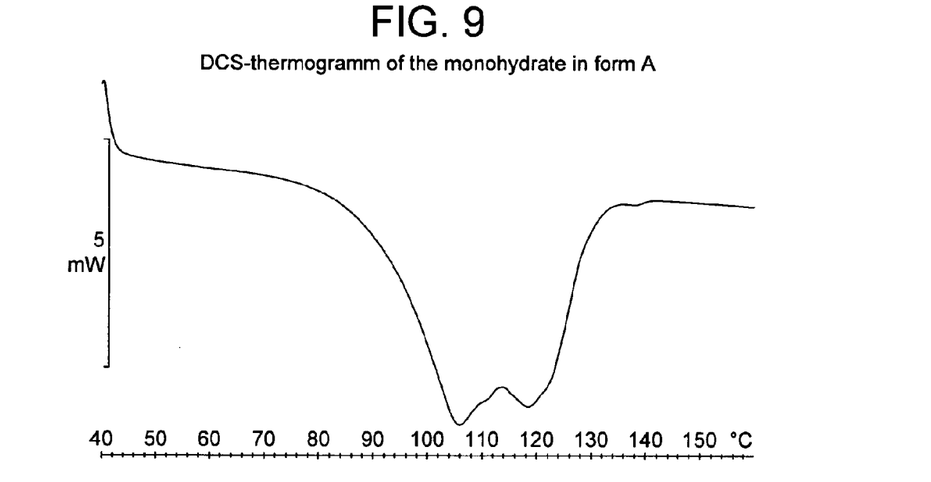

Characteristic for the monohydrate in form A is also the thermogram in DSC (see FIG. 9), which has typically a broad endothermic signal in the range from 50° C. to 130° C.—depending on purity and experimental conditions. Such a broad signal is characteristically different from the signal of modification I, which—also in pure form—has a sharp peak typically at around 140° C. (see FIG. 6). As mentioned above, both measurements were carried out as described for modification C of the racemic syn-compound of formula (I).

The present invention preferably relates to the monohydrate in form A of the racemic anti-compound of formula (I), wherein said form is characterized by an x-ray powder diffraction pattern, expressed in terms of d-spacings and relative intensities, wherein said an x-ray powder diffraction pattern comprises the following characteristic lines: 6.81 Å (weak), 6.39 Å (weak), 6.08 Å (weak), 5.50 Å (weak), 5.33 Å (strong), 4.90 Å (weak), 4.43 Å (medium), 4.25 Å (weak), 4.07 Å (weak), 3.96 Å (medium), 3.84 Å (medium), 3.61 Å (weak) and 3.47 Å (weak).

The present invention preferably relates to the monohydrate in form A of the racemic anti-compound of formula (I), wherein said form is characterized by having the x-ray powder diffraction pattern depicted in FIG. 7.

In one embodiment of the invention, the monohydrate in form A of the racemic anti-compound of formula (I) has in the thermogram in differential scanning calorimetry an endothermic signal in the range from 50° C. to 130° C.

In one embodiment of the invention the monohydrate in form A of the racemic anti-compound of formula (I) is in substantially pure form. According to the invention "substantially pure" means preferably at least 75% by weight of the monohydrate in form A of the racemic anti-compound of formula (I), more preferably at least 80% by weight. The chemical nature of the material, which is not the monohydrate in form A of the racemic anti-compound of formula (I), will depend on the production and/or purification method and at least part of it can be, for example, the racemic syn-compound of formula (I), which can be present in solid solution in the crystal matrix of the anti-compound or in the form of individual crystalline or amorphous material.

In another embodiment of the present invention, the monohydrate in form A of the racemic anti-compound of formula (I) is in pure form. According to the invention "pure" means at least 90% by weight of the monohydrate in form A of the racemic anti-compound of formula (I), more preferably at least 95% by weight, even more preferably at least 98% by weight.

Compositions Comprising Racemic Syn- and Anti-Compounds of Formula (I) in Novel Solid Forms:

The large-scale production of racemic syn- or anti-compounds of formula (I) having high purities, such as a purity of at least 98% by weight of the racemic syn-compound of formula (I), is associated with significant costs. As both syn- and anti-compounds have fungicidal activity, it can be desirable under cost/performance-considerations to produce a mixture-product comprising both compounds. Such mixture-products are typically enriched in either the syn- or the anti-compound. An example of a highly syn-enriched mixture-product is a mixture having a syn/anti-ratio ranging from 80:20 to 95:5. Another example of a highly syn-enriched mixture-product is a mixture having a syn/anti-ratio ranging from 80:20 to 85:15.

It is another goal of the invention to provide a highly syn-enriched composition comprising the racemic syn-compound of formula (I) in solid form and the racemic anti-compound of formula (I) in solid form, which has good properties in relation to the formulation of the composition and its storability either as solid material or in typical formulations used in agrochemistry, such as a suspension concentrate (SC).

Therefore the present invention relates further to a composition comprising the racemic syn-compound of formula (I) in solid form and the racemic anti-compound of formula (I) in solid form, wherein the ratio of the racemic syn- to the racemic anti-compound of formula (I) ranges from 80:20 to 95:5, preferably form 80:20 to 90:10, more preferably form 80:20 to 85:15, even more preferably is about 85:15, wherein the racemic syn-compound of formula (I) is in crystal modification C as described above and wherein at least a part of the racemic anti-compound of formula (I) is a monohydrate in form A as described above.

Figure 10A:
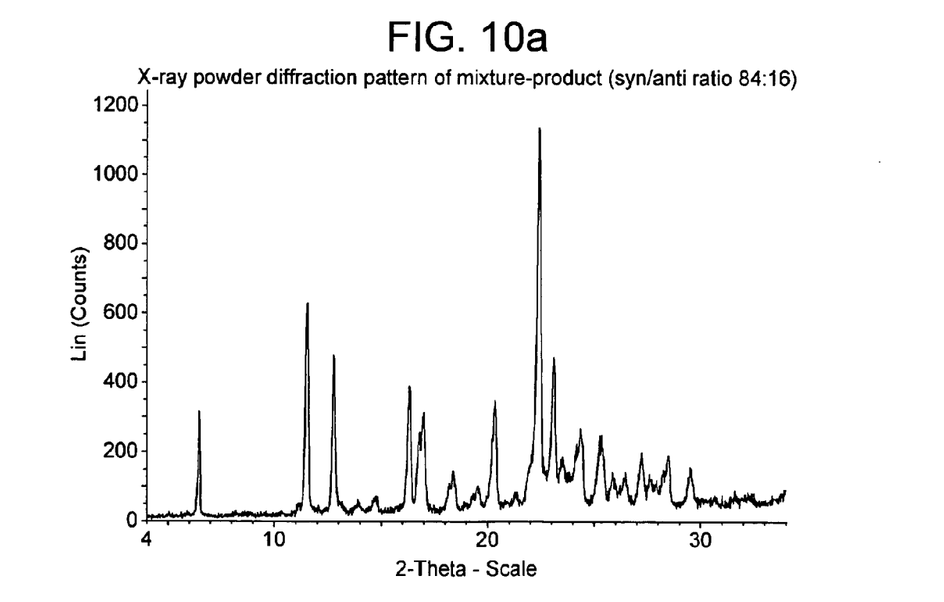
FIG. 10a shows the x-ray pattern and FIG. 11 shows the DSC-plot of the mixture of the racemic syn-compound of formula (I) in modification C and the monohydrate of the racemic anti-compound of formula (I) in form A (syn/anti-ratio 84:16) as prepared in example P4.
Figure 10B:
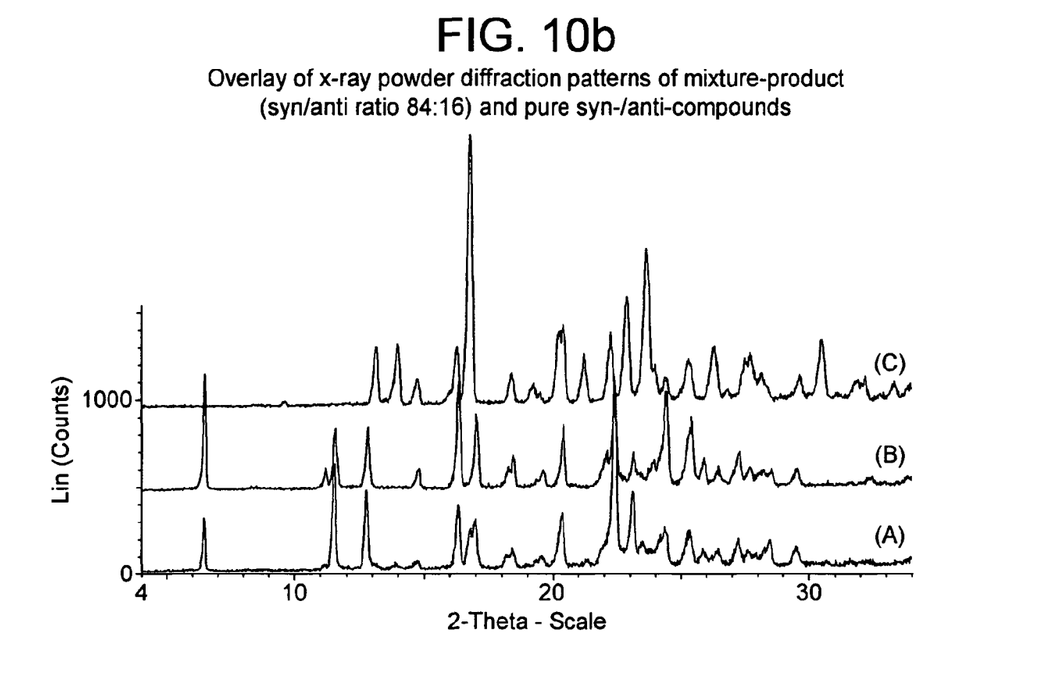
FIG. 10b shows an overlay of x-ray patterns of:
(A) the mixture as prepared in example P4,
(B) the pure racemic syn-compound of formula (I) in modification C as prepared in example P1 (FIG. 10b, trace B, is identical to FIG. 1), and
(C) the pure monohydrate of the racemic anti-compound of formula (I) in form A as prepared in example P3 (FIG. 10b, trace C is identical to FIG. 7).
Figure 11:
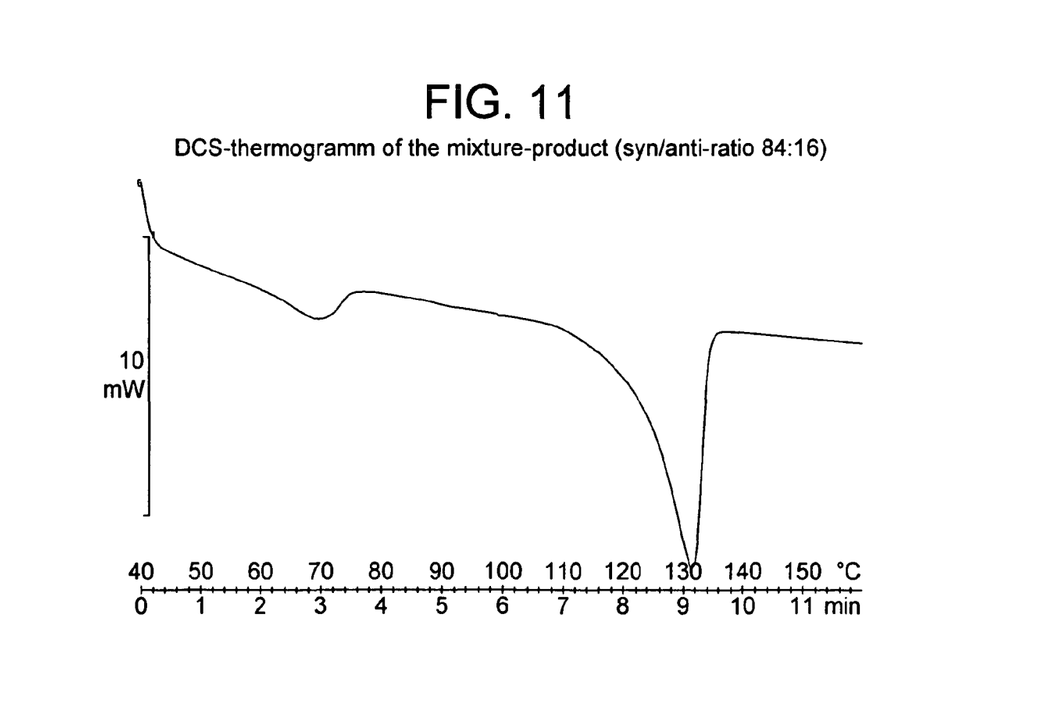

An example of such a composition (syn/anti-ratio=84:16) was prepared via different intermediate polymorphic forms, which were solubilized in methanol/water (9:1) and re-crystallized, as described in example P4 (see also FIGS. 10 and 11).

The method as laid out in example P4b) was repeated starting from a crystalline material of a compound of formula (I) with a syn/anti-ratio of 88:12 (prepared by the method as laid out in example P4a), purity: 94.6%). Also from this starting material a composition comprising the racemic syn-compound of formula (I) in crystal modification C and the racemic anti-compound of formula (I) as a monohydrate in form A could be obtained.

Figure 12A:
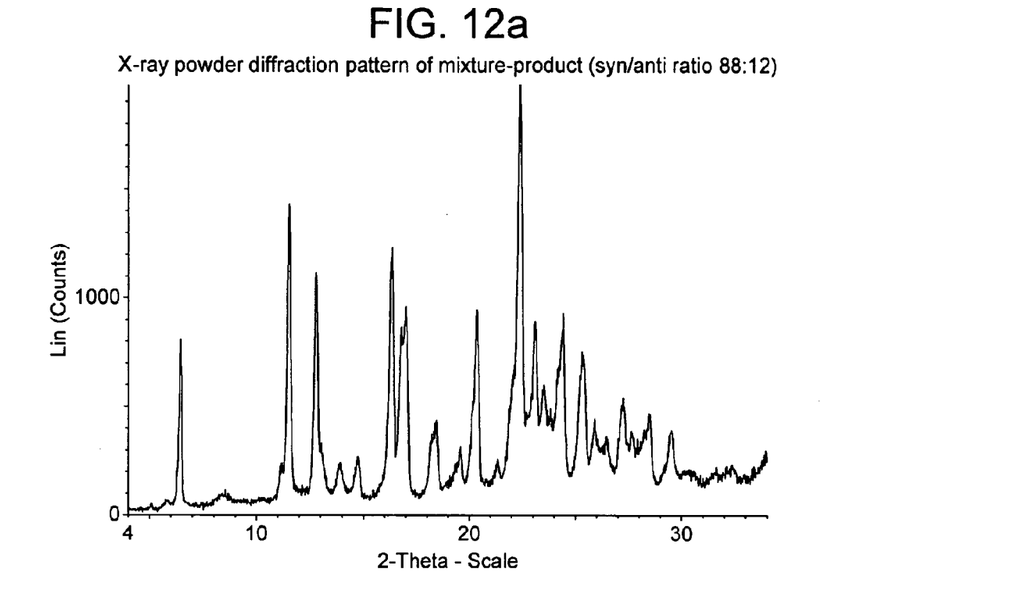
FIG. 12a shows the x-ray pattern and FIG. 13 shows the DSC plot of the mixture of the racemic syn-compound of formula (I) in modification C and the monohydrate of the racemic anti-compound of formula (I) in form A (syn/anti-ratio 88:12) as prepared in example P5.
Figure 12B:
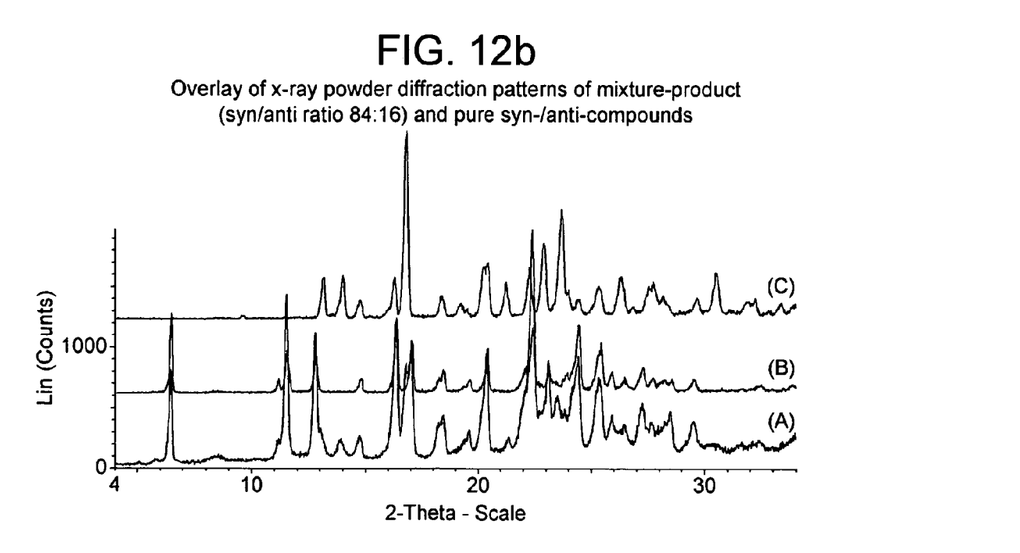
FIG. 12b shows an overlay of x-ray patterns of:
(A) the mixture as prepared in example P5,
(B) the pure racemic syn-compound of formula (I) in modification C as prepared in example P1 (FIG. 12b, trace B, is identical to FIG. 1), and
(C) the pure monohydrate of the racemic anti-compound of formula (I) in form A as prepared in example P3 (FIG. 12b, trace C, is identical to FIG. 7).
Figure 13:
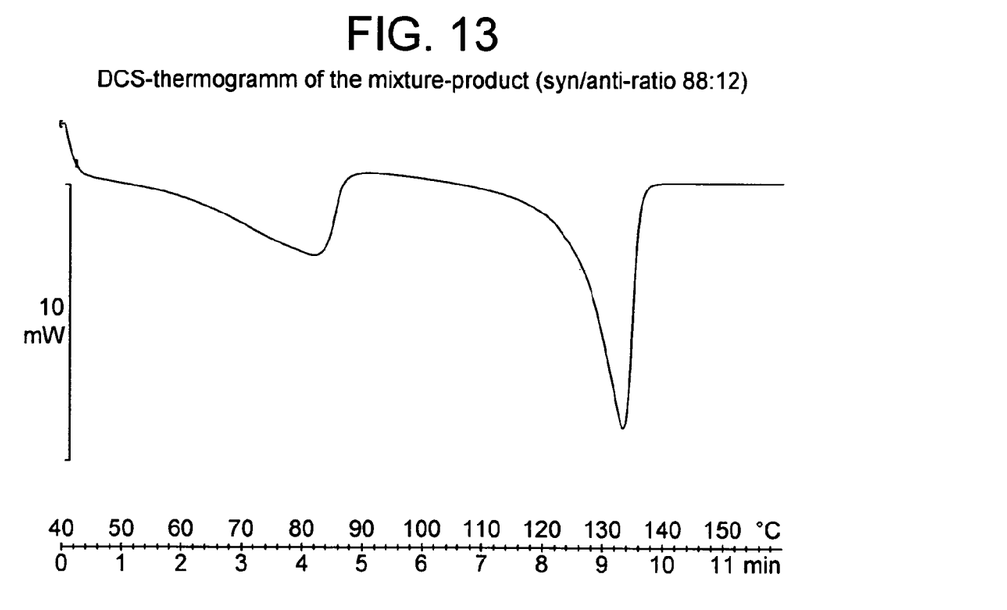

A further composition (syn/anti-ratio=88:12) was prepared via different polymorphic forms, which were suspended in aceton/water (3:7 by weight) and re-crystallized ("crystal transformation method"), as it is described in example P5 (see also FIGS. 12 and 13).

Accordingly, the invention relates further to a process for preparing a composition comprising racemic syn-3-difluoromethyl-1-methyl-1H-pyrazole-4-carboxylic acid (9-isopropyl-1,2,3,4-tetrahydro-1,4-methano-naphthalen-5-yl)-amide in solid form and racemic anti-3-difluoromethyl-1-methyl-1H-pyrazole-4-carboxylic acid (9-isopropyl-1,2,3,4-tetrahydro-1,4-methano-naphthalen-5-yl)-amide in solid form, wherein the ratio of the syn-amide to the anti-amide ranges from 80:20 to 95:5, preferably form 80:20 to 90:10, wherein the syn-amide is in crystal modification C as described above and wherein at least part of the anti-amide is a monohydrate in form A as described above, which comprises (a) preparing a solution or a suspension of the syn-amide and the anti-amide, wherein the ratio of the syn-amide to the anti-amide ranges from 80:20 to 95:5, preferably form 80:20 to 90:10, in a solvent or a suspending agent, (b) crystallizing the desired composition from the solvent or suspending agent by adding seed crystals in the form of:
  (b1) the syn-amide in crystal modification C as described above, or
  (b2) a mixture of the syn-amide in crystal modification C as described above and
    of the monohydrate in form A of the anti-amide as described above, and (c) isolating the desired composition.

According to the invention the term "novel solid forms of the compound of formula (I)" is used to address modification C of the racemic syn-compound of formula (I), modification I of the racemic anti-compound of formula (I), the monohydrate in form A of the racemic anti-compound of formula (I) or any mixtures of these solid forms.

All novel solid forms of the compound of formula (I) can be used against microorganisms, that cause diseases on useful plants, in particular against phytopathogenic fungi. They are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: pome fruits; stone fruits; grapes; strawberries; tomatoes; potatoes; peppers; lettuce; sugarbeets; peanuts; wheat; rye; barley; triticale; oats; rice; maize; cotton; soybeans; oilseed rape; pulse crops; sunflower; coffee; tea; sugarcane; banana; vegetables, such as cucumbers, beans and cucurbits; tobacco; fruit and ornamentals in horticulture and viticulture; turf and lawns.

The term "useful plants" is to be understood as including also (1) plants that have been rendered tolerant to herbicides like bromoxynil or classes of herbicides as a result of conventional methods of breeding or genetic engineering; (2) plants which have been so transformed by the use of recombinant DNA techniques that they are capable of synthesising one or more selectively acting toxins, such as are known, for example, from toxin-producing bacteria, especially those of the genus Bacillus; (3) plants which have been so transformed by the use of recombinant DNA techniques that they are capable of synthesising antipathogenic substances having a selective action, such as, for example, the so-called "pathogenesis-related proteins"; and (4) plants which may also comprise one or more "output traits" (traits which provide enhanced product quality), such as traits which alter the fatty acid composition of the plant/seed, for example provide altered levels of oleic acid and/or stearic acid or traits which provide industrial products such as, for example, pharmaceuticals (including antibodies) and also industrial enzymes (e.g. phytase, xylanase, glucanase).

All novel solid forms of the compound of formula (I) are also effective to protect natural substances of plant and/or animal origin, their processed forms or technical material against attack of fungi.

The amount of the novel solid forms of the compound of formula (I) to be applied, will depend on various factors, such as the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

The novel solid forms of the compound of formula (I) can also be used together with further fungicides, bactericides, herbicides, insecticides, nematicides, molluscicides or mixtures of several of those active ingredients.

The novel solid forms of the compound of formula (I) may be employed in any conventional form, for example in the form of a suspension concentrate (SC), an emulsion concentrate (EC) or a flowable concentrate for seed treatment (FS). When using the novel solid forms of the compound of formula (I), they are applied to the useful plants, the locus thereof or propagation material thereof, typically as a composition (a conventional form) as described above. In one embodiment of the invention, the novel solid forms of the compound of formula (I) are employed in the form of a suspension concentrate (SC).

The novel solid forms of the compound of formula (I) can be applied to the fungi, the useful plants, the locus thereof or the propagation material thereof. They may be applied before or after infection of the useful plants or the propagation material thereof by the fungi. The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing. The term "plant propagation material" is understood to denote generative parts of a plant, such as seeds, which can be used for the multiplication of the latter, and vegetative material, such as cuttings or tubers, for example potatoes; preferably "plant propagation material" denotes seeds.

The novel solid forms of the compound of formula (I) are useful for controlling the following plant diseases on useful plants: *Alternaria* species in fruit and vegetables; *Ascochyta* species in pulse crops; *Botrytis cinerea* in strawberries, tomatoes, sunflower, pulse crops, vegetables and grapes, such as *Botrytis cinerea* on grape; *Cercospora arachidicola* in peanuts; *Cochliobolus sativus* in cereals; *Colletotrichum* species in pulse crops; *Erysiphe* species in cereals; such as *Erysiphe graminis* on wheat and *Erysiphe graminis* on barley; *Erysiphe cichoracearum* and *Sphaerotheca fuliginea* in cucurbits; *Fusarium* species in cereals and maize; *Gaumannomyces graminis* in cereals and lawns; *Helminthosporium* species in maize, rice and potatoes; *Hemileia vastatrix* on coffee; *Microdochium* species in wheat and rye; *Mycosphaerella fijiensis* in banana; *Phakopsora* species in soybeans, such as *Phakopsora pachyrizi* in soybeans; *Puccinia* species in cereals, broadleaf crops and perennial plants; such as *Puccinia recondita* on wheat, *Puccinia striiformis* on wheat and *Puccinia recondita* on barley; *Pseudocercosporella* species in cereals, such as *Pseudocercosporella herpotrichoides* in wheat; *Phragmidium mucronatum* in roses; *Podosphaera* species in fruits; *Pyrenophora* species in barley, such as *Pyrenophora teres* on barley; *Pyricularia oryzae* in rice; *Ramularia collo*-cygni in barley; *Rhizoctonia* species in cotton, soybean, cereals, maize, potatoes, rice and lawns, such as *Rhizoctonia solani* on potato, rice, turf and cotton; *Rhynchosporium secalis* on barley, *Rhynchosporium secalis* on rye; *Sclerotinia* species in lawns, lettuce, vegetables and oil seed rape, such as *Sclerotinia sclerotiorum* on oilseed rape and *Sclerotinia homeocarpa* on turf; *Septoria* species in cereals, soybean and vegetables, such as *Septoria tritici* on wheat, *Septoria nodorum* on wheat and *Septoria* glycines on soybean; *Sphacelotheca reilliana* in maize; *Tilletia* species in cereals; *Uncinula necator*, *Guignardia bidwellii* and *Phomopsis viticola* in vines; *Urocystis occulta* in rye; *Uromyces* species in beans; *Ustilago* species in cereals and maize; *Venturia* species in fruits, such as *Venturia inequalis* on apple; *Monilinia* species on fruits; and/or *Penicillium* species on citrus and apples.

When applied to the useful plants, the novel solid forms of the compound of formula (I) are used at rates of 5 to 2000 g a.i./ha, particularly 10 to 1000 g a.i./ha, e.g. 50, 75, 100 or 200 g a.i./ha; when applied in the form of a composition, the application rate typically range from 20 to 4000 g of total composition per hectare. When used for treating seed, rates of 0.001 to 50 g of modification C per kg of seed, preferably from 0.01 to 10 g per kg of seed are generally sufficient.

The present invention furthermore relates to a fungicidal composition comprising as active ingredient the novel solid forms of the compound of formula (I) in a fungicidally effective amount together with a suitable carrier.

These compositions of the invention may be employed in any conventional form, wherein at least a part of the compound of formula (I) is in the solid state, for example in the form of a twin pack (KK or KL), a suspension concentrate (SC), a suspo-emulsion (SE), a water dispersible granule (WG), an emulsifiable granule (EG), an emulsifiable powder (EP), an oil dispersion (OD), an oil miscible flowable (OF), an ultra-low volume suspension (SU), a wettable powder (WP), a technical concentrate (TK), a dispersible concentrate (DC), a powder for dry seed treatment (DS), a flowable concentrate for seed treatment (FS), a water dispersible powder for seed treatment (WS) or any technically feasible formulation, wherein at least a part of the compound of formula (I) is in the solid state, in combination with agriculturally acceptable adjuvants. Preferably the composition is in the form of a suspension concentrate (SC).

Such compositions may be produced in a conventional manner, e.g. by mixing the active ingredient or active ingredients with appropriate formulation inerts (diluents, solvents, fillers and optionally other formulating ingredients such as surfactants, biocides, anti-freeze, stickers, thickeners and compounds that provide adjuvancy effects). Particularly formulations to be applied in spraying forms, such as water dispersible concentrates (e.g. SC, DC, SE, and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol. These compositions may also comprise further pesticides, such as, for example, fungicides, insecticides or herbicides.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art.

In general, the formulations include from 0.01 to 90% by weight of the active agent, from 0 to 20% agriculturally acceptable surfactant and 10 to 99.99% solid or liquid formulation inerts and adjuvant(s), the active agent being at least the modification C, and optionally comprising other active agents. Concentrated forms of compositions generally contain in between about 2 and 80%, preferably between about 5 and 70% by weight of active agent. Application forms of the compositions may for example contain from 0.01 to 20% by weight, preferably from 0.01 to 5% by weight of active agent. Whereas commercial products will preferably be formulated as concentrates, the end user will normally employ diluted formulations.

The present invention furthermore relates to a method of controlling diseases on useful plants or on propagation material thereof caused by phytopathogens, which comprises applying to the useful plants, the locus thereof or propagation material thereof a composition comprising as active ingredient novel solid forms of the compound of formula (I) in a fungicidally effective amount together with a suitable carrier.

The preparations of the novel solid forms of the compound of formula (I) are carried out, for example, as described in the embodiments below.

EXAMPLE P1

Preparation of the Syn-Compound of the Formula (I) (purity: >99%) in Modification C a1) Preparation of the Pure Racemic Syn-Compound of Formula (I) via Fractional Crystallization 240 g of crystalline 3-difluoromethyl-1-methyl-1H-pyrazole-4-carboxylic acid (9-isopropyl-1,2,3,4-tetrahydro-1,4-methano-naphthalen-5-yl)-amide (purity: 97.6%; syn/anti ratio 94:6; prepared starting from 9-isopropyl-5-amino-benzonorbornene with a syn/anti ratio 9:1 as described in WO 04/35589 or WO 06/37632) was mixed with 560 g methanol at a temperature of 60° C. The mixture was heated to 65° C. and stirred until the crystalline material was dissolved. The solution was cooled over a time period of 20 minutes to a temperature of 40° C. and then over a time period of 2 hours to 25° C. During that time period a precipitate was formed. The precipitate was filtered at 25° C. and dried at 60° C. under vacuum. 113 g of pure syn-3-difluoromethyl-1-methyl-1H-pyrazole-4-carboxylic acid (9-isopropyl-1,2,3,4-tetrahydro-1,4-methano-naphthalen-5-yl)-amide (purity: >99%, m.p. 128° C., yield: 47%) was obtained. The crystalline material was analyzed by differential scanning calorimetry and x-ray diffraction and was identified as crystal modification B of syn-3-difluoromethyl-1-methyl-1H-pyrazole-4-carboxylic acid (9-isopropyl-1,2,3,4-tetrahydro-1,4-methano-naphthalen-5-yl)-amide; no presence of modification A or C was detected.

a2) Preparation of the Pure Racemic Syn-Compound of Formula (I) Via Chromatography syn-Enriched 5-amino-9-isopropyl-benzonorbornene (49.83 g, syn/anti ratio 9:1; prepared as described in WO 04/35589 or WO 06/37632) was chromatographed on silica gel (4.7 kg) in ethyl acetate-hexane-(1:6). The first eluting fractions with syn-contents >98% (g.l.c) were combined (5.80 g) and crystallized from hexane to give crystals (4.40 g, 8.8%, m.p. 57-58° C.) with a syn-content of 99.8% (g.l.c). 5-Amino-9-syn-isopropyl-benzonorbornene (7.32 g, 99.8% syn, prepared as described above) was reacted with 5-difluoromethyl-2-methyl-pyrazole-4-carboxylic acid (8.33 g, 1.3 eq., prepared as described in WO 04/35589), bis-(2-oxo-3-oxazolidinyl)-phosphinic acid chloride (12.96 g, 1.4 eq.) and triethylamine (9.2 g, 2.5 eq.) in dichloromethane (100 ml) at room temperature for 21 h to give after aqueous work up with saturated NaHCO$_3$-solution and purification on silica gel in ethyl acetate-hexane-(2:3) a viscous oil. Crystallization from hexane afforded the desired product (12.1 g, 92.6%, m.p. 128-130° C., 99.2% syn (g.l.c)).

b) Preparation of the Racemic Syn-Compound of Formula (I) in Modification C 14 mg of crystalline syn-3-difluoromethyl-1-methyl-1H-pyrazole-4-carboxylic acid (9-isopropyl-1,2,3,4-tetrahydro-1,4-methano-naphthalen-5-yl)-amide having a purity >99% prepared as described above was mixed with 0.4 ml o-xylene. The mixture was heated to 40° C. until the crystalline material was dissolved, the solution was kept for 2 hours at 40° C. The solution was cooled to 5° C. with a cooling rate of 10° C./hour and then kept at 5° C. for 10 hours. During that time period a precipitate was formed. Excess solvent was removed and the crystals were dried by a nitrogen gas stream. Syn-3-difluoromethyl-1-methyl-1H-pyrazole-4-carboxylic acid (9-isopropyl-1,2,3,4-tetrahydro-1,4-methano-naphthalen-5-yl)-amide (purity: >99%, m.p. 141° C.) was obtained. The crystalline material was analyzed by differential scanning calorimetry and x-ray diffraction and was identified as crystal modification C of syn-3-difluoromethyl-1-methyl-1H-pyrazole-4-carboxylic acid (9-isopropyl-1,2,3,4-tetrahydro-1,4-methano-naphthalen-5-yl)-amide no presence of modification A or B was detected (see FIGS. 1, 2 and 3).

EXAMPLE P2

Preparation of the Racemic Anti-Compound of Formula (I) in Modification I anti-Enriched 5-amino-9-isopropyl-benzonorbornene (42 g, syn/anti-ratio 3:7; prepared as described in WO 04/35589 or WO 06/37632) was chromatographed on silica gel (2.1 kg) in ethyl acetate-hexane-(1:7). The last eluting fractions with anti-contents >97% (1.2 g, g.l.c) were combined and rechromatographed on silica gel (250 g) in ethyl acetate to give 0.72 g (1.96%) of a crystalline solid (m.p. 64° C.) with an anti-content of 99.2% (g.l.c).

5-Amino-9-anti-isopropyl-benzonorbornene (0.72 g, 99.2% anti, prepared as described above) was reacted with 5-difluoromethyl-2-methyl-pyrazole-4-carboxylic acid (0.76 g, 1.2 eq.), bis-(2-oxo-3-oxazolidinyl)-phosphinic acid chloride (1.0 g, 1.2 eq.) and triethylamine (0.87 g, 2.4 eq.) in dichloromethane (25 ml) at room temperature for 3 h to give after aqueous work up with saturated NaHCO$_3$-solution and purification on silica gel in ethyl acetate-hexane-(1:2) a viscous oil. Crystallization from hexane afforded the desired product (1.18 g, yield: 91.7%, m.p. 140° C., 99.4% anti (g.l.c)). The crystalline material was analyzed by differential scanning calorimetry and x-ray diffraction and was identified as crystal modification I of anti-3-difluoromethyl-1-methyl-1H-pyrazole-4-carboxylic acid (9-isopropyl-1,2,3,4-tetrahydro-1,4-methano-naphthalen-5-yl)-amide no presence of other crystalline forms was detected (see FIGS. 4, 5 and 6).

EXAMPLE P3

Preparation of the Monohydrate of the Racemic Anti-Compound of Formula (I) in Modification A 75 mg of crystalline anti-3-difluoromethyl-1-methyl-1H-pyrazole-4-carboxylic acid (9-isopropyl-1,2,3,4-tetrahydro-1,4-methano-naphthalen-5-yl)-amide having a purity >99% prepared as described above was mixed with 1 ml of water/methanol (1:4 mixture by weight) at a temperature of 45° C. and sonicated until the material was dissolved to a clear solution. The solution was kept at a temperature of 45° C. for 10 minutes. During that time period a precipitate was formed. Excess solvent was removed and the crystals were dried by a nitrogen gas stream. A crystalline material of anti-3-difluoromethyl-1-methyl-1H-pyrazole-4-carboxylic acid (9-isopropyl-1,2,3,4-tetrahydro-1,4-methano-naphthalen-5-yl)-amide (purity: >99%) was obtained. The crystalline material was analyzed by differential scanning calorimetry and x-ray diffraction and was identified as the monohydrate of anti-3-difluoromethyl-1-methyl-1H-pyrazole-4-carboxylic acid (9-isopropyl-1,2,3,4-tetrahydro-1,4-methano-naphthalen-5-yl)-amide in form A. No presence of other crystalline forms was detected (see FIGS. 7, 8 and 9).

EXAMPLE P4

Preparation of a Mixture of the Racemic Syn-Compound of Formula (I) in Modification C and of the Monohydrate of the Racemic Anti-Compound of Formula (I) in Form A (Syn/Anti-Ratio 84:16) Via Crystallization from a Solution a) Preparation of the Compound of Formula (I)

To a solution of 203 kg of 9-isopropyl-5-amino-benzonorbornene (syn/anti-ratio 84:16, prepared as described in WO 04/35589 or WO 06/37632; 0.42 kmol, 46% chlorobenzene solution) and 47 kg of triethylamine (0.46 kmol, 1.1 equivalents) in 145 kg of chlorobenzene there are added at 40° C., in the course of 2 hours, 201 kg of 3-difluoromethyl-1-methyl-1H-pyrazole-4-carbonyl chloride (47% chlorobenzene solution, 0.42 kmol, 1 equivalent) and stirring is carried out for 15 minutes. After the addition of water and hydrochloric acid (a pH of 6-7 is established), the organic phase is extracted with chlorobenzene. The organic phase is concentrated by distilling off chlorobenzene. Following subsequent crystallisation from methanol/water (3:1 mixture by weight), 142 kg of 3-difluoromethyl-1-methyl-1H-pyrazole-4-carboxylic acid (9-isopropyl-1,2,3,4-tetrahydro-1,4-methano-naphthalen-5-yl)-amide are obtained (m.p. 113-114° C.; purity: 93.8%; syn/anti-ratio 84:16 according to GC, yield: 88.6%). The crystalline material was analyzed by differential scanning calorimetry and x-ray diffraction and was identified as crystal modification A of syn-3-difluoromethyl-1-methyl-1H-pyrazole-4-carboxylic acid (9-isopropyl-1,2,3,4-tetrahydro-1,4-methano-naphthalen-5-yl)-amide, no presence of other crystalline material could be detected. On the basis of this data (e.g. no individual crystalline anti-material was detected) it is likely that the racemic anti-compound of formula (I) was in solid solution in the crystal matrix of the racemic syn-compound of formula (I).

b) Preparation of a Mixture of the Racemic Syn-Compound of Formula (I) in Modification C and of the Monohydrate of the Racemic Anti-Compound of Formula (I) in Form A 2 g of the crystalline material prepared as described under P4a) above was mixed with 12 g of methanol/water (9:1 mixture by weight). The mixture was heated to 50° C. and stirred until the crystalline material was dissolved and the solution was stirred for 2 hours at 40° C. The solution was cooled to 10° C. with a cooling rate of 15° C./hour C. Once a temperature of 36° C. has been reached 0.1 g of the racemic syn-compound of formula (I) in crystal modification C (prepared as described in P1 above) was added. The mixture was then kept at 10° C. for 48 hours. During that time period the desired precipitate was formed. Excess solvent was removed and the crystals were dried by a nitrogen gas stream. A crystalline material was obtained.

The crystalline material was analyzed by differential scanning calorimetry and x-ray diffraction and was identified as a mixture of the racemic syn-compound of formula (I) in modification C and of the monohydrate of the racemic anti-compound of formula (I) in form A. No presence of further crystal forms was detected (see FIGS. 10*a*, 10*b* and 11).

From the comparison of the x-ray pattern for the material (see FIG. 10*b*, trace A) with the x-ray pattern of modification C (see FIG. 10*b*, trace B) it is clear that a second crystalline material is present due to the additional peaks/peak-shoulders. The additional peaks at 2-Theta of 13.96, 16.81, 21.23 and 23.68 and the shoulder at 13.08 can be associated with characteristic peaks belonging to the monohydrate in form A (see FIG. 10*b*, trace C). On the contrary, no additional peak that can be associated with modification I (see FIG. 4) is visible; especially the strong peak at 2-Theta of 5.46 is absent.

The DSC-thermogramm (see FIG. 11) shows a melting endotherm with a sharp peak around 132° C.—characteristic for modification C—and a broad endothermic signal in the range from 50° C. to 75° C.—again characteristic for the monohydrate in form A.

EXAMPLE P5

Preparation of a Mixture of the Racemic Syn-Compound of Formula (I) in Modification C and of the Monohydrate of the Racemic Anti-Compound of Formula (I) in Form A (Syn/Anti-Ratio 88:12) Via Crystallization from a Suspension The starting material was crystalline material being a mixture of the racemic syn-compound of formula (I) in crystal modifications A and B prepared as described above (syn-anti-ratio 88:12, purity: 96%, as laid out in example P4a) above, also for this material it was likely that the anti-compound was in solid solution in the matrices of the syn-compound).

431 kg of the starting material was suspended in 2443 kg of acetone/water (3:7 mixture by weight). The suspension was heated to 40° C. and seeded with a suspension of 3 kg of a mixture of the racemic syn-compound of formula (I) in crystal modification C and the monohydrate of the racemic anti-compound of formula (I) in form A (syn/anti ratio 88:12, prepared by the method as laid out in example P4b)) was added in 17 kg of acetone/water (3:7 mixture by weight). The suspension was stirred for 6 hours at 40° C. During that time period the desired precipitate was formed. The suspension was cooled to 25° C. with a cooling rate of 15° C./hour. The suspension was kept at 25° C. for 1 hour. The precipitate was filtered at 25° C. and dried at 40° C. 391 kg of crystalline material was obtained (syn/anti-ratio: 88:12, purity: 94%).

The crystalline material was analyzed by differential scanning calorimetry and x-ray diffraction and was identified as a mixture of the racemic syn-compound of formula (I) in modification C and of the monohydrate of the racemic anti-compound of formula (I) in form A. No presence of further crystal forms was detected (see FIGS. 12a, 12b and 13).

As for example P4: from the comparison of the x-ray pattern for the material (see FIG. 12b, trace A) with the x-ray pattern of modification C (see FIG. 12b, trace B) it is clear that a second crystalline material is present due to the additional peaks/peak-shoulders. The additional peaks at 2-Theta of 13.96, 16.81, 21.23 and 23.68 and the shoulder at 13.08 can be associated with characteristic peaks belonging to the monohydrate in form A (see FIG. 12b, trace C). On the contrary, no additional peak that can be associated with modification I (see FIG. 4) is visible; especially the strong peak at 2-Theta of 5.46 is absent.

The DSC-thermogramm (see FIG. 13) is also very similar to the thermogramm of the material of example P4. It shows a melting endotherm with a sharp peak around 132° C.—characteristic for modification C—and a broad endothermic signal in the range from 50° C. to 90° C.—again characteristic for the monohydrate in form A.

FORMULATION EXAMPLES

The examples which follow serve to illustrate the invention, "active ingredient" denoting a novel solid form of the compound of formula (I).

Suspension Concentrates

| | |
|---|---|
| active ingredient | 40% |
| propylene glycol | 10% |
| nonylphenol polyethylene glycol ether | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the other formulation components, giving a suspension concentrate which can be diluted in water at any desired rate. Using such dilutions, living plants as well as plant propagation material can be treated and protected against infestation by microorganisms, by spraying, pouring or immersion.

Wettable Powders

| | a) | b) |
|---|---|---|
| active ingredient | 25% | 75% |
| sodium lignosulfonate | 5% | — |
| sodium lauryl sulfate | 3% | 5% |
| sodium diisobutylnaphthalenesulfonate | — | 10% |
| highly dispersed silicic acid | 5% | 10% |
| kaolin | 62% | — |

The active ingredient is thoroughly mixed with the other formulation components and the mixture is thoroughly ground in a suitable mill, affording wettable powders that can be diluted with water to give suspensions of the desired concentration.

Powders for Dry Seed Treatment

| | a) | b) |
|---|---|---|
| active ingredient | 25% | 75% |
| light mineral oil | 5% | 5% |
| highly dispersed silicic acid | 5% | — |
| kaolin | 65% | — |
| talc | — | 20% |

The active ingredient is thoroughly mixed with the other formulation components and the mixture is thoroughly ground in a suitable mill, affording powders that can be used directly for seed treatment.

Dustable Powders

| | a) | b) |
|---|---|---|
| active ingredient | 5% | 6% |
| talc | 95% | — |
| kaolin | — | 94% |

Ready-for-use dusts are obtained by mixing the active ingredient with the carriers and grinding the mixture in a suitable mill. Such powders can also be used for dry dressings for seed.

Extruded Granules

| | % w/w |
|---|---|
| active ingredient | 15-80 |
| sodium lignosulfonate | 2-10 |
| sodium alkyl naphthalene sulfonate | 2-5 |
| kaolin | 5-81 |

The active ingredient is mixed and ground with the other formulation components, and the mixture is moistened with water. The mixture is extruded and then dried in a stream of air.

Flowable Concentrates for Seed Treatment

| | |
|---|---|
| active ingredient | 40% |
| propylene glycol | 5% |
| copolymer butanol PO/EO | 2% |
| Tristyrylphenol ethoxylate | 2% |
| 1,2-benzisothiazolin-3-one | 0.5% |
| monoazo-pigment calcium salt | 5% |
| silicone oil (in the form of a 75% emulsion in water) | 0.2% |
| water | 45.3% |

The finely ground active ingredient is intimately mixed with the other formulation components, giving a suspension concentrate which can be diluted further in water to be applied to seeds. Using such dilutions, plant propagation material can be treated and protected against infestation by microorganisms, by spraying, pouring or immersion.

DESCRIPTION OF FIGURES

FIG. 1 shows the x-ray pattern.

FIG. 4 shows the x-ray pattern.

FIG. 7 shows the x-ray pattern.

What is claimed is:

1. Crystal modification C of racemic syn-3-difluoromethyl-1-methyl-1H-pyrazole-4-carboxylic acid (9-isopropyl-1,2,3,4-tetrahydro-1,4-methano-naphthalen-5-yl)-amide, wherein said crystal modification is characterized by an x-ray powder diffraction pattern, expressed in terms of d-spacings and relative intensities, wherein said an x-ray powder diffraction pattern comprises the following characteristic lines: 13.74 Å (strong), 7.95 Å (weak), 6.94 Å (medium), 6.04 Å (weak), 4.43 Å (medium) and 3.72 Å (strong).

2. The crystal modification of claim 1 further characterized by having the x-ray powder diffraction pattern depicted in FIG. 1.

3. The crystal modification of claim 1 further characterized by having in the thermogram in differential scanning calorimetry an endothermic signal with a peak in the range from 130° C. to 142° C.

4. The crystal modification of claim 1 in substantially pure form.

5. Crystal modification I of racemic anti-3-difluoromethyl-1-methyl-1H-pyrazole-4-carboxylic acid (9-isopropyl-1,2,3,4-tetrahydro-1,4-methano-naphthalen-5-yl)-amide, wherein said crystal modification is characterized by an x-ray powder diffraction pattern, expressed in terms of d-spacings and relative intensities, wherein said an x-ray powder diffraction pattern comprises the following characteristic lines: 16.19 Å (very strong), 11.77 Å (strong), 9.47 Å (medium), 5.49 Å (very strong), 5.16 Å (medium), 4.61 Å (strong) and 4.22 Å (strong).

6. The crystal modification of claim 5 further characterized by having the x-ray powder diffraction pattern depicted in FIG. 4.

7. The crystal modification of claim 5 in substantially pure form.

8. Monohydrate in form A of racemic anti-3-difluoromethyl-1-methyl-1H-pyrazole-4-carboxylic acid (9-isopropyl-1,2,3,4-tetrahydro-1,4-methano-naphthalen-5-yl)-amide, wherein said form is characterized by an x-ray powder diffraction pattern, expressed in terms of d-spacings and relative intensities, wherein said an x-ray powder diffraction pattern comprises the following characteristic lines: 6.39 Å (weak), 6.08 Å (weak), 5.33 Å (strong), 4.07 Å (weak), 3.84 Å (medium) and 3.47 Å (weak).

9. The monohydrate as defined in claim 8 further characterized by having the x-ray powder diffraction pattern depicted in FIG. 7.

10. The monohydrate as defined in claim 8 further characterized by having in the thermogram in differential scanning calorimetry an endothermic signal in the range from 50° C. to 130° C.

11. The monohydrate as defined in claim 8 in substantially pure form.

12. A composition comprising racemic syn-3-difluoromethyl-1-methyl-1H-pyrazole-4-carboxylic acid (9-isopropyl-1,2,3,4-tetrahydro-1,4-methano-naphthalen-5-yl)-amide in solid form and racemic anti-3-difluoromethyl-1-methyl-1H-pyrazole-4-carboxylic acid (9-isopropyl-1,2,3,4-tetrahydro-1,4-methano-naphthalen-5-yl)-amide in solid form, wherein the ratio of the syn-amide to the anti-amide ranges from 80:20 to 95:5,
wherein the syn-amide is in crystal modification C characterized by an x-ray powder diffraction pattern, expressed in terms of d-spacings and relative intensities, wherein said an x-ray powder diffraction pattern comprises the following characteristic lines: 13.74 Å (strong), 7.95 Å (weak), 6.94 Å (medium), 6.04 Å (weak), 4.43 Å (medium) and 3.72 Å (strong);
and wherein at least part of the anti-amide is a monohydrate in form A characterized by an x-ray powder diffraction pattern, expressed in terms of d-spacings and relative intensities, wherein said an x-ray powder diffraction pattern comprises the following characteristic lines: 6.39 Å (weak), 6.08 Å (weak), 5.33 Å (strong), 4.07 Å (weak), 3.84 Å (medium) and 3.47 Å (weak).

13. A composition for control of diseases on useful plants or on propagation material thereof caused by phytopathogens, that comprises as active ingredient at least a solid material selected from:
the crystal modification C of racemic syn-3-difluoromethyl-1-methyl-1H-pyrazole-4-carboxylic acid (9-isopropyl-1,2,3,4-tetrahydro-1,4-methano-naphthalen-5-yl)-amide characterized by an x-ray powder diffraction pattern, expressed in terms of d-spacings and relative intensities, wherein said an x-ray powder diffraction pattern comprises the following characteristic lines:

13.74 Å (strong), 7.95 Å (weak), 6.94 Å (medium), 6.04 Å (weak), 4.43 Å (medium) and 3.72 Å (strong);

the crystal modification I of racemic anti-3-difluoromethyl-1-methyl-1H-pyrazole-4-carboxylic acid (9-isopropyl-1,2,3,4-tetrahydro-1,4-methano-naphthalen-5-yl)-amide characterized by an x-ray powder diffraction pattern, expressed in terms of d-spacings and relative intensities, wherein said an x-ray powder diffraction pattern comprises the following characteristic lines: 16.19 Å (very strong), 11.77 Å (strong), 9.47 Å (medium), 5.49 Å (very strong), 5.16 Å (medium), 4.61 Å (strong) and 4.22 Å (strong);

the monohydrate in form A of racemic anti-3-difluoromethyl-1-methyl-1H-pyrazole-4-carboxylic acid (9-isopropyl-1,2,3,4-tetrahydro-1,4-methano-naphthalen-5-yl)-amide characterized by an x-ray powder diffraction pattern, expressed in terms of d-spacings and relative intensities, wherein said an x-ray powder diffraction pattern comprises the following characteristic lines: 6.39 Å (weak), 6.08 Å (weak), 5.33 Å (strong), 4.07 Å (weak), 3.84 Å (medium) and 3.47 Å (weak); and the composition as defined in claim 12;

in a fungicidally effective amount together with a suitable carrier.

* * * * *